United States Patent
Yeo et al.

(10) Patent No.: US 7,672,703 B2
(45) Date of Patent: Mar. 2, 2010

(54) ELECTRODE FOR MEASURING ELECTROCARDIOGRAM AND ELECTROCARDIOGRAM DEVICE INCLUDING THE SAME

(75) Inventors: Hyung-sok Yeo, Yongin-si (KR); Jin-sang Hwang, Suwon-si (KR); Wan-taek Han, Hwaseong-si (KR); Kun-soo Shin, Seongnam-si (KR); Youn-ho Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 896 days.

(21) Appl. No.: 11/403,920

(22) Filed: Apr. 14, 2006

(65) Prior Publication Data
US 2006/0276715 A1    Dec. 7, 2006

(30) Foreign Application Priority Data
Jun. 7, 2005    (KR) .................... 10-2005-0048400

(51) Int. Cl.
*A61B 5/0408*   (2006.01)
*A61B 5/0402*   (2006.01)
*A61B 5/04*     (2006.01)

(52) U.S. Cl. ............... 600/391; 600/382; 600/386; 607/142; 607/149; 607/152; 607/153

(58) Field of Classification Search ............ 607/142, 607/149, 152, 153; 600/382, 386, 391
See application file for complete search history.

(56) References Cited

U.S. PATENT DOCUMENTS 5,824,033 A * 10/1998 Ferrari ................. 607/142

FOREIGN PATENT DOCUMENTS

KR    0278492 Y1    6/2002

OTHER PUBLICATIONS

Masayuki Ohyama, et al., "Active Wireless Electrodes for Surface Electromyography", 18th Annual International Conference of the IEEE Engineering in Medicine and Biology Society, 1996, pp. 295-296.

* cited by examiner

*Primary Examiner*—Carl H Layno
*Assistant Examiner*—Yun Haeng Lee
(74) *Attorney, Agent, or Firm*—Sughrue Mion, PLLC

(57) ABSTRACT

An electrode for measuring an electrocardiogram. The electrode comprises a signal detector operable to detect an electrocardiogram signal. An electrolytic gel is coated onto a first surface of the signal detector. The gel is electrically conductive and operable to adhere to a skin. A connector is electrically connected to the signal detector.

16 Claims, 9 Drawing Sheets

(a)

(b)

ELECTRODE FOR MEASURING ELECTROCARDIOGRAM AND ELECTROCARDIOGRAM DEVICE INCLUDING THE SAME

CROSS-REFERENCE TO RELATED PATENT APPLICATIONS

This application claims the priority of Korean Patent Application No. 10-2005-0048400, filed on Jun. 7, 2005, in the Korean Intellectual Property Office, the disclosure of which is incorporated herein in its entirety by reference.

BACKGROUND OF THE INVENTION

1. Field of the Invention

The present invention relates to an electrode for measuring an electrocardiogram and an electrocardiogram device including the electrode, and more particularly, to an electrode for measuring an electrocardiogram, which is robust against motion artifacts, and an electrocardiogram measuring device including the electrode.

2. Description of the Related Art

An electrocardiogram is a recording of an action current produced by contraction and expansion of cardiac muscles, which is measured by attaching an electrode to the surface of the body. The active potentials generated during systole and diastole cause electrical currents to propagate from the heart to the rest of the body, the electrical currents generate a potential difference between different parts of the body, and the potential difference is measured and recorded through a surface electrode attached to the skin of the body. The electrocardiogram is used to detect whether there is a problem in the heart, and is importantly used for diagnosis of heart disease, such as angina pectoris, myocardial infraction, and arrhythmia, as a basic diagnostic element.

In general, a device for measuring the electrocardiogram includes an electrode that contacts the skin and measures the active potential, a power supply, and a controller that interprets and processes the measured active potential signal.

The device for measuring the electrocardiogram may be a wireless or wired device. A wired device for measuring an electrocardiogram, which is generally used in a hospital, has an electrode that contacts the skin and is connected to the power supply and the controller. The wireless device for measuring the electrocardiogram includes an electrode that contacts the skin, a power supply, a controller, and a transceiver that transmits and receives a signal.

The electrode is classified as a wet-type electrode or a dry-type electrode according to whether the electrode includes an electrolyte. The dry-type electrode is placed on a region of the chest using an elastic band. However, there is chest pressure when the dry-type electrode is placed on the thorax, and therefore a device including the dry-type electrode is not desirable to be used for a long period of time. Further, if the electrode is initially loosely attached to a user or the humidity of the electrode is lowered by long-term use of the electrode, the quality of a signal may be deteriorated.

Meanwhile, the wet type electrode does not require an additional band, but uses adhesive materials. FIG. 1(a) is a bottom view of the conventional wet type electrode, and FIG. 1(b) is a top view of the conventional wet type electrode. The bottom view represents a skin contact surface, and the top view represents a controller contact surface. Referring to FIG. 1A, the skin contact surface of the conventional wet type electrode is formed by a signal detector 102 and a skin contact portion 104. The signal detector 102 is covered with an electrolytic gel, and the skin contact portion 104 is covered with an adhesive material. Referring to FIG. 1B, the controller contact surface is formed by a controller connector 106 and the skin contact portion 104.

The conventional wet type electrode uses the adhesive material, which induces pain and loss of hair from the skin when the electrode is detached from the skin. Moreover, since the adhesion of the electrode is lowered as time passes, the electrode is detached from the skin and easily exposed to the outside, and consequently the quality of the signal is deteriorated by drying of the electrolyte or breaking of the conductivity between the electrode and the skin. Therefore, the wet type electrode is not suitable to be used for a long period of time. Further, since the skin contact portion is enlarged to improve the adhesion between the electrode and the skin and the signal detector is relatively small in the total area of the electrode, the device including the wet type electrode cannot robustly deal with motion artifacts due to the movements of the body.

There are several conventional inventions related to the electrocardiogram measurement device. For example, Japanese Patent Laid-open Gazette No. 2001-269322 discloses a signal measurement device which includes a base sheet having a circuit unit that acquires an electrocardiogram and transmits and receives an electrocardiogram signal measured by an electrode is placed on the thorax of the body. Additionally, U.S. Pat. No. 5,862,803 discloses a device for diagnosis and monitoring, which includes a semiconductor chip having an electrode that includes a transceiver and a battery and is integrated on the semiconductor chip and is attached to the skin of a patient. However, the conventional inventions use the conventional wet type or dry type electrodes, and thus cannot solve the above problems.

SUMMARY OF THE INVENTION

The present invention provides an electrode which deals with motion artifacts, acquires good signal quality, does not induce pain or loss of hair from the body when the electrode is detached from the skin, and can be used in an electrocardiogram measuring device.

The present invention also provides an electrocardiogram measuring device including the electrode.

According to an aspect of the present invention, there is provided an electrode for measuring an electrocardiogram. The electrode comprises a signal detector operable to detect an electrocardiogram signal. An electrolytic gel is coated onto a first surface of the signal detector. The gel is electrically conductive and operable to adhere to a skin. A controller connector is electrically connected to the signal detector.

According to another aspect of the present invention, there is provided an electrode for measuring an electrocardiogram comprising an adhesive portion having a surface coated with an adhesive material operable to be attached to the skin. A plurality of signal detectors are disposed apart from each other. Each of said plurality of signal detectors has a first surface connected to the surface of the adhesive portion. The first surface of the signal detector has a smaller area than the adhesive portion. An electrolytic gel is coated on a second surface of each signal detector. The electrolytic gel is operable to adhere to the skin and is electrically conductive. A plurality of controller connectors are electrically connected to the respective plurality of signal detectors.

According to still another aspect of the present invention, there is provided an electrocardiogram measuring device comprising: the above electrode including the plurality of signal detectors; and a controller which has a plurality of electrode connectors detachably electrically connected to the respective controller connectors of the electrode.

According to yet another aspect of the present invention, there is provided an electrocardiogram measuring device comprising: the above electrode including the plurality of signal detectors; a controller which has a plurality of electrode connectors detachably electrically connected to the respective controller connectors of the electrode and a power supply connector; and a power supply which has a controller connector detachably electrically connected to the power supply connector of the controller.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art.

The present invention relates to an electrode for measuring an electrocardiogram. Exemplary embodiments of the electrode for measuring an electrocardiogram are shown in FIGS. 2-6.

Figure 1:
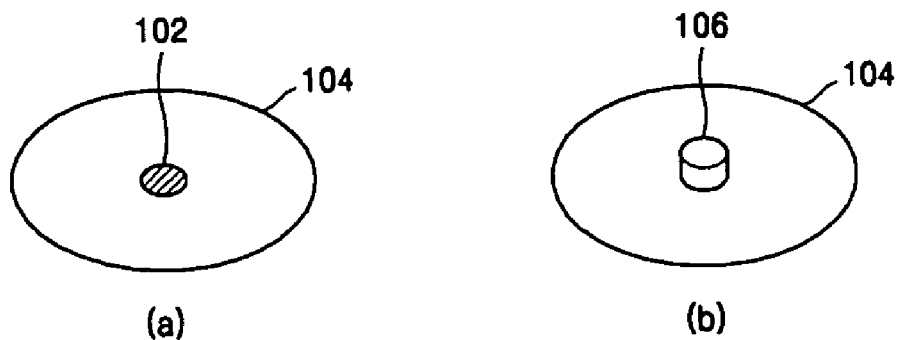
FIG. 1 shows a bottom surface and a top surface of a conventional electrode (A: bottom surface, B: top surface)
Figure 2:
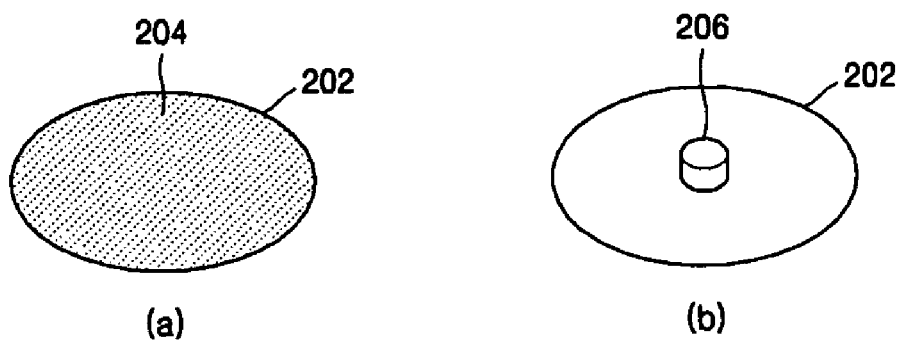
FIG. 2 shows a bottom surface and a top surface of an electrode according to an embodiment of the present invention (A: bottom surface, B: top surface)

FIG. 2 shows a bottom surface (a) and a top surface (b) of an electrode for measuring an electrocardiogram according to an embodiment of the present invention. Referring to FIG. 2, the electrode for measuring an electrocardiogram includes a signal detector 202 that measures an electrocardiogram signal, electrolytic gel 204 that is coated on one surface of the signal detector 202 and adheres to the skin and is electrically conductive, and a controller connector 206 that is electrically connected to the signal detector 202.

The signal detector 202 may be fabricated from the same material as the conventional electrode. For example, the signal detector 202 may be composed of one selected from a group consisting of platinum, gold, silver, copper, and palladium.

According to the electrode of the present embodiment, the area of the signal detector 202 is larger than the area of the conventional signal detector. Therefore, the electrode with the above structure is robust against motion artifacts, and thus obtains good signal quality.

Since the adhesive electrolytic gel 204 having electric conductivity is coated on the entire surface of the signal detector 202, the signal detector 202 can occupy the whole area of the electrode. That is, in the conventional electrode, a skin adhering portion is large and the area of the signal detector is small to improve the adhesive strength between the electrode and skin. On the other hand, the electrode according to the present invention can enlarge the signal detector 202 by using the electrolytic gel 204 having excellent skin adhesion and electric conductivity.

The electrolytic gel 204 may contain 30 to 70 weight percent of water, 0.5 to 5 weight percent of tartaric acid, 20 to 50 weight percent of concentrated glycerine, 5 to 10 weight percent of sodium polyacrylate, and 1 to 6 weight percent of polyethylene glycol.

In the electrolytic gel 204 of the present embodiment, water contributes to the conductivity, and hydrates and softens the horny layer of the skin to promote transdermal absorption of electrolytic ingredients. When the electrolytic gel 204 contains not more than 30 percent by weight of water, the skin hydrating effect is reduced, and when the electrolytic gel 204 contains not less than 70 percent by weight of water, the viscosity of the gel is lowered.

The tartaric acid controls the pH of the electrolytic gel 204, and keeps the electrolyte stable or the absorption condition of the electrolytic ingredients on the skin. The electrolytic gel 204 may have a pH of between 4.5 and 7.0. When the electrolytic gel 204 contains not more than 0.5 percent by weight of tartaric acid, the stability of the electrolyte or the absorption condition of the electrolytic ingredients on the skin is deteriorated, and when the electrolytic gel 204 contains not less than 5 percent by weight of tartaric acid, the adhesiveness of the gel 204 is lowered.

The concentrated glycerine maintains moisture, and affects flexibility, adhesiveness, periodical stabilization after dampproofing, and conductivity. When the electrolytic gel 204 contains not more than 20 percent by weight of concentrated glycerine, the retainment of moisture, flexibility and adhesiveness are reduced, and when the electrolytic gel 204 contains not less than 50 percent by weight of concentrated glycerine, the conductivity is lowered.

The sodium polyacrylate maintains the moisture content, increases the stabilization, and improves the transdermal adhesion. Also, the sodium polyacrylate prevents the electrolytic gel 204 from being tacky or drooping, helps alleviate pain when removing the electrode and prevents the electrolytic gel 204 from remaining on the skin when the electrode is detached from the skin. When the electrolytic gel 204 contains not more than 5 percent by weight of polyacrylate, the adhesion is reduced, the removal pain is increased, and the electrolytic gel 204 remains on the skin when the electrode is detached from the skin. On the other hand, when the electrolytic gel 204 contains not less than 10 percent by weight of polyacrylate, the conductivity is lowered.

The polyethylene glycol dissolves the electrolytic ingredients in the electrolytic gel 204 uniformly, or diffuses the electrolytic ingredients in the electrolytic gel 204 so that the electrolytic ingredients are stably maintained in the electrolytic gel 204 and released into the skin, and the transdermal absorption is promoted. Further, the polyethylene glycol prevents the conductive material of the electrolytic gel 204 from being crystallized and separated from the gel 204, which boosts the transdermal absorption. When the electrolytic gel 204 contains not more than 1 percent by weight of polyethylene glycol, the electrolyte is crystallized and separated from the electrolytic gel 204, and when the electrolytic gel 204 contains not less than 6 percent by weight of polyethylene glycol, the feeling of the electrolytic gel 204 against the skin is uncomfortable.

It is desirable that the electrolytic gel 204 may contain 60.5 percent by weight of water, 1.0 percent by weight of tartaric acid, 31.0 percent by weight of concentrated glycerine, 6.0 percent by weight of sodium polyacrylate and 1.5 percent by weight of polyethylene glycol.

The electrolytic gel 204 in which the adhesion between the electrode and the skin and the conductivity are considered does not deteriorate the signal quality, alleviates discomfort when the electrode is detached from the skin, and does not damage the skin when the electrode is attached to the skin for a long time.

Figure 3:
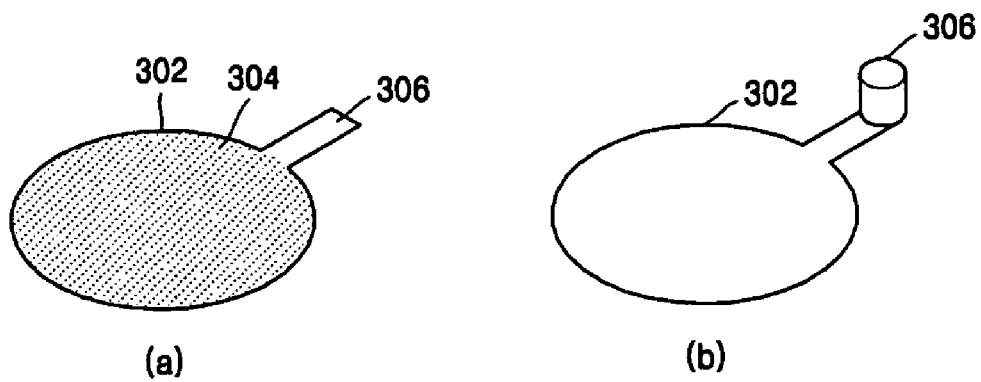
FIG. 3 shows a bottom surface and a top surface of an electrode according to another embodiment of the present invention (A: bottom surface, B: top surface)

FIG. 3 shows a bottom surface (a) and a top surface (b) of an electrode for measuring an electrocardiogram according to another embodiment of the present invention. Referring to FIG. 3, like the electrode of FIG. 2, the electrode for measuring an electrocardiogram includes a signal detector 302; electrolytic gel 304 which is coated onto one surface of the signal detector 302, adheres to the skin and is electrically conductive; and a controller connector 306 electrically connected to the signal detector 302. However, the position of the controller connector 306 is different from the position of the controller connector 206 of FIG. 2. That is, the forms of the elements of the present invention can be varied.

Figure 4:
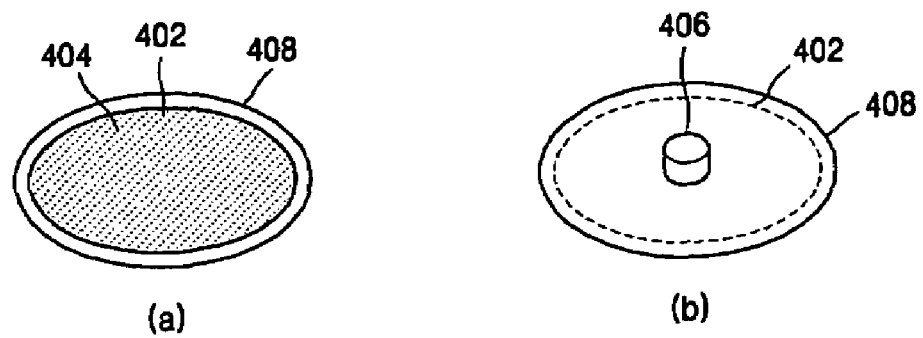
FIG. 4 shows a bottom surface and a top surface of an electrode according to still another embodiment of the present invention (A: bottom surface, B: top surface)

FIG. 4 shows a bottom surface (a) and a top surface (b) of an electrode for measuring an electrocardiogram according to still another embodiment of the present invention ((a): bottom view, (b): top view). Referring to FIG. 4, the electrode for measuring an electrocardiogram includes a signal detector 402 that detects the electrocardiogram signal; electrolytic gel 404 which is coated on one surface of the signal detector 402, adheres to the skin and is electrically conductive; a controller connector 406 electrically connected to the signal detector 402; and an adhesive portion 408 of which one surface coated with an adhesive material is attached to the other surface of the signal detector 402 where the electrolytic gel 404 is not coated and which is larger than the signal detector 402 so that the adhesive portion 408 can be attached to the skin.

The adhesive portion 408 may be made of non-woven fabric.

If the electrode is attached to the skin for a long time, the electrode may be separated from the skin due to various motions of the body, and due to the separation of the electrode, external air and impurities may be inserted in the electrolytic gel 404, which results in drying of the electrolyte or breaking of the conductivity between the electrode and the skin. However, when the adhesive portion 408 is additionally included in the electrode, such drying of the electrolyte or breaking of the conductivity can be prevented.

Figure 5:
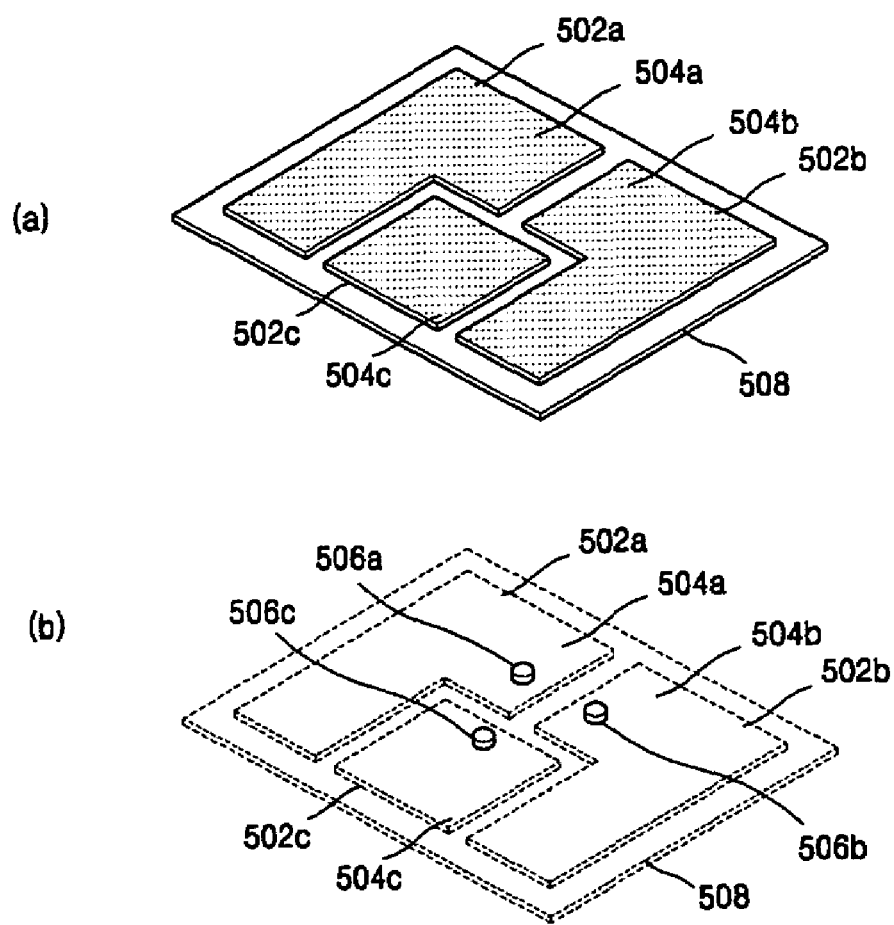
FIG. 5 shows a bottom surface and a top surface of an electrode according to yet another embodiment of the present invention (A: bottom surface, B: top surface)

FIG. 5 shows a bottom surface (a) and a top surface (b) of an electrode for measuring an electrocardiogram according to yet another embodiment of the present invention. Referring to FIG. 5, the electrode is a multiple electrode including a plurality of signal detectors 502a, 502b and 502c. The electrode includes an adhesive portion 508 of which one surface is coated with an adhesive material to be attached to the skin; the signal detectors 502a, 502b and 502c, which are disposed apart from each other, each having one surface connected to the surface of the adhesive portion 508 on which the adhesive material is coated, and each of which is smaller than the adhesive portion 508 and detects an electrocardiogram signal; electrolytic gels 504a, 504b and 504c which are coated on the other surface of each signal detectors 502a, 502b, and 502c, adhere to the skin and are electrically conductive; and controller connectors 506a, 506b and 506c electrically connected to the signal detectors 502a, 502b and 502c, respectively.

The adhesive portion 508 may be made of non-woven fabric.

Each of the signal detectors 502a, 502b and 502c may be fabricated from the same material as the conventional electrode. For example, the signal detectors 502a, 502b and 502c may be composed of one selected from the group consisting of platinum, gold, silver, copper, and palladium.

The electrolytic gels 504a, 504b and 504c may contain 30 to 70 weight percent of water, 0.5 to 5 weight percent of tartaric acid, 20 to 50 weight percent of concentrated glycerine, 5 to 10 weight percent of sodium polyacrylate, and 1 to 6 weight percent of polyethylene glycol.

Figure 6:
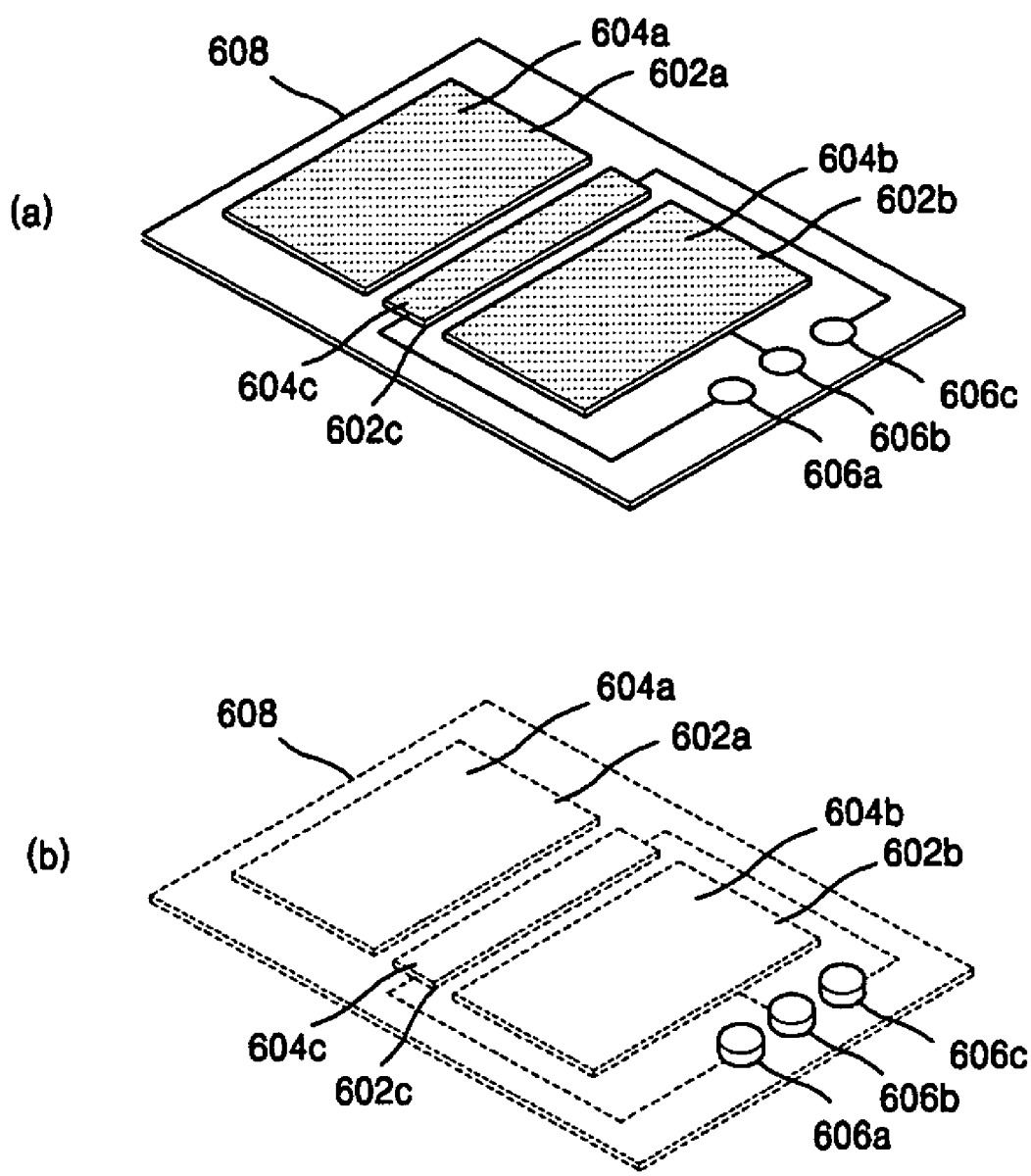
FIG. 6 shows a bottom surface and a top surface of an electrode according to another embodiment of the present invention (A: bottom surface, B: top surface)

FIG. 6 shows a bottom surface (a) and a top surface (b) of an electrode including a plurality of signal detectors 602a, 602b, and 602c for measuring an electrocardiogram according to another embodiment of the present invention. Referring to FIG. 6, like the electrode of FIG. 5, the electrode includes an adhesive portion 608 of which one surface is coated with an adhesive material to be attached to the skin; the signal detectors 602a, 602b and 602c, which are disposed apart from each other, each having one surface connected to the surface of the adhesive portion 608 on which the adhesive material is coated, and each of which is smaller than the adhesive portion 608 and detects an electrocardiogram signal; electrolytic gels 604a, 604b and 604c which are coated on the other surface of each signal detectors 602a, 602b, and 602c, adhere to the skin and are electrically conductive; and controller connectors 606a, 606b and 606c electrically connected to the signal detectors 602a, 602b and 602c, respectively. However, the positions of the signal detectors 602a, 602b and 602c and controller connectors 606a, 606b and 606c are different from the positions of the signal detectors 502a, 502b and 502c and controller connectors 506a, 506b and 506c. That is, the forms of the elements of the present invention can be varied.

The effect of motion artifacts generated during daily movement and exercise on baseline drift of an electrocardiograph measured by the electrode according to the present invention and on baseline drift of an electrocardiograph measured by the conventional electrode were tested and compared. Among the evaluation result, the standard deviation of the baseline drift is shown in Table 1.

TABLE 1

| Motion artifact | Electrode according to the present invention (diameter: 40 mm) | Conventional electrode (diameter: 10 mm) | Evaluation |
| --- | --- | --- | --- |
| Turning of body | 0.11 V | 1.80 V | Present electrode superior to conventional electrode |
| 4 km/h | 0.10 V | 0.29 V | Present electrode superior to conventional electrode |
| 6 km/h | 0.11 V | 0.53 V | Present electrode superior to conventional electrode |
| 8 km/h | 0.12 V | 0.48 V | Present electrode superior to conventional electrode |

As shown in Table 1, the electrode according to the present invention is more robust against motion artifacts than the conventional electrode.

Figure 7:
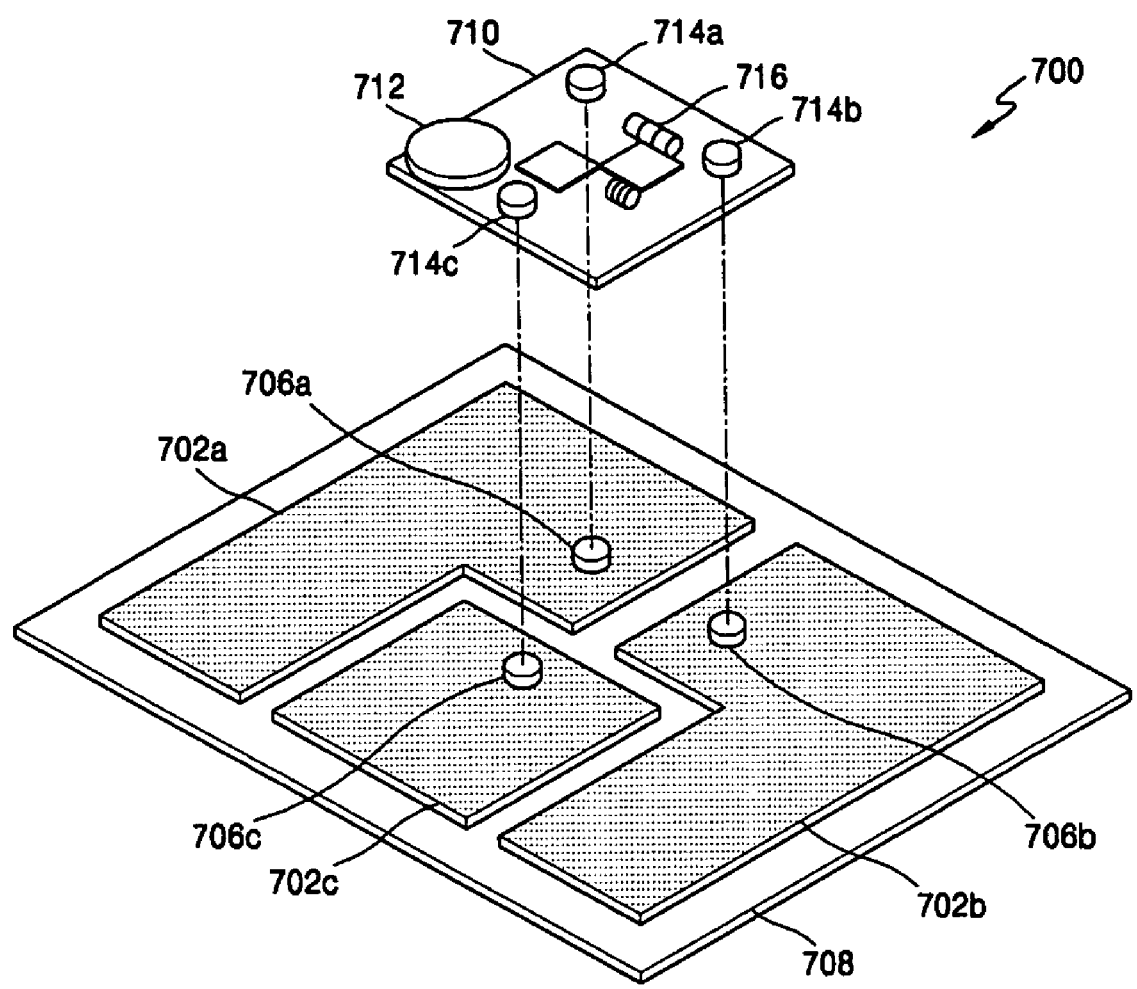
FIG. 7 shows an electrocardiogram measurement device according to an embodiment of the present invention.
Figure 8:
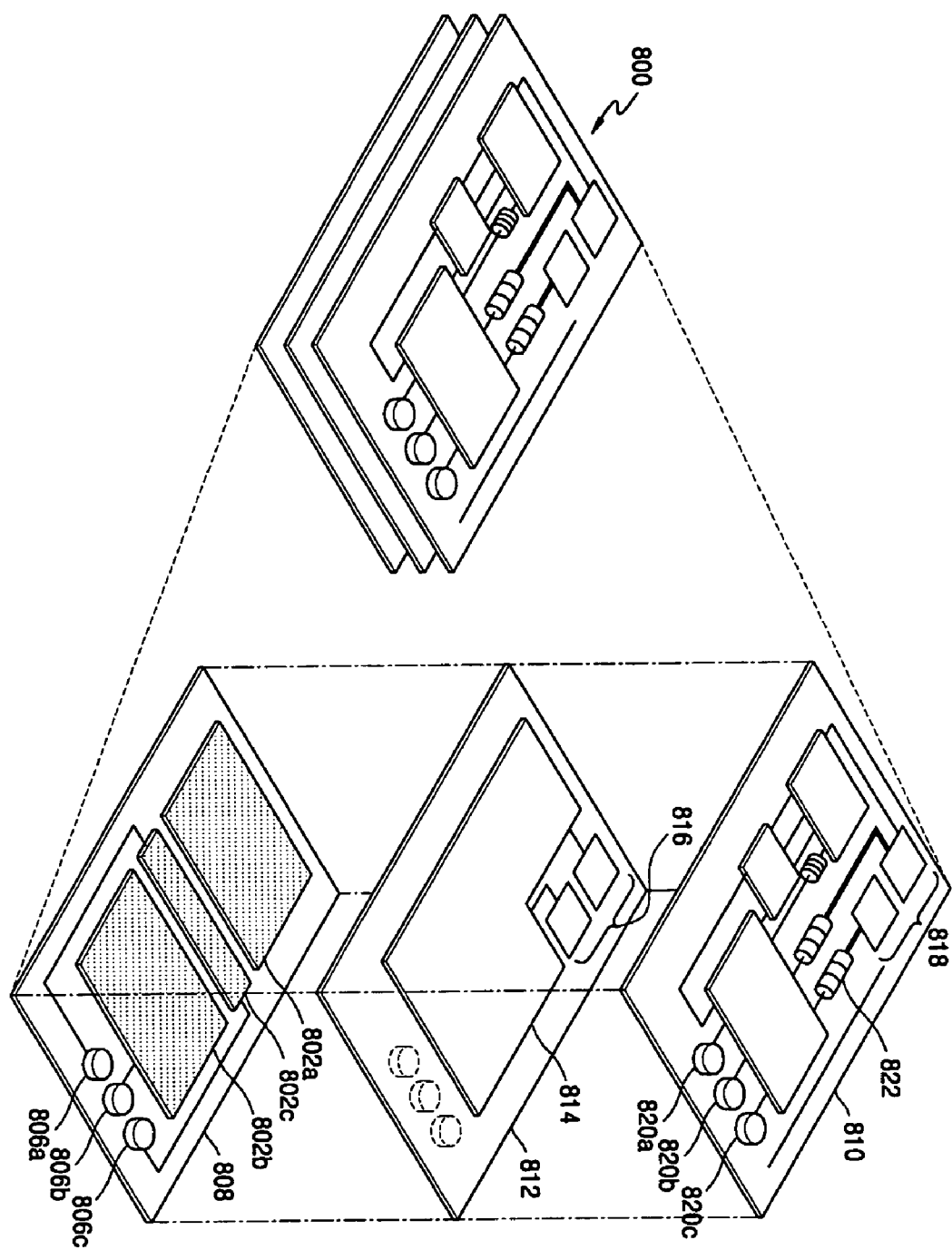
FIG. 8 shows an electrocardiogram measurement device according to another embodiment of the present invention.

The present invention relates to an electrocardiogram measuring device including the above electrode. The electrocardiogram measuring device may include a single electrode having a signal detector, or may desirably include multiple electrodes having a plurality of signal detectors which are integrated with each other. FIGS. 7 and 8 show electrocardiogram devices 700 and 800 according to embodiments of the present invention.

Referring to FIG. 7, the electrocardiogram measurement device 700 includes a multiple electrode according to the present invention; and a controller 710 which has a plurality of controller connectors 706a, 706b and 706c of the electrode and a plurality of electrode connectors 714a, 714b and 714c which are detachably electrically connected to the respective controller connectors 706a, 706b and 706c of the electrode and are disposed on the electrode.

The plurality of controller connectors 706a, 706b and 706c are positioned to correspond to the electrode connectors 714a, 714b and 714c, respectively, and therefore detachably connected to each other. The detachable connection between the controller connectors 706a, 706b and 706c and the electrode connectors 714a, 714b and 714c can be implemented using any detachable connecting method, for example, using female screws and male screws.

The controller 710 may include a power supply 712. Also, the controller 720 may include a signal transceiver 716.

The controller 710 may be a flexible printed circuit board (PCB). The flexible circuit board can be attached to and conform to the curves of the human body.

FIG. 8 shows an electrocardiogram device 800 according to another embodiment of the present invention. Referring to FIG. 8, the electrocardiogram device 800 includes a multiple electrode according to the present invention; a controller 810 which includes a plurality of electrode connectors 820a, 820b and 820c detachably electrically connected to respective controller connectors 806a, 806b and 806c included in the multiple electrode and a power supply connector 818 and is disposed on the multiple electrode; and a power supply 812 which includes a controller connector 816 detachably electrically connected to the power supply connector 818 and is disposed on or below the controller 810.

The plurality of controller connectors 806a, 806b and 806c of the multiple electrode are positioned to correspond to the respective electrode connectors 820a, 820b and 820c of the controller 810 and the power supply connector 818 of the controller 810 is positioned to correspond to the controller connector 816 of the power supply 812. Therefore the multiple electrode 808 and the controller 810 can be detachably connected to each other. These detachable connections can be implemented using any available methods, for example, using female screws and male screws.

The controller 810 may include a signal transceiver 822. The controller 810 may be a flexible printed circuit board. The flexible board can be attached to and conform to the curves of the human body.

As described above, the electrocardiogram measuring device 700 including the multiple electrode and the controller 710 and the electrocardiogram measuring device 800 including the multiple electrode, the controller 810, and the power supply 812 are integrated devices which can be attached to the skin. When the multiple electrode, the controller 810, or the power supply 812 of the device 800 needs to be replaced, they can be individually separated from the device 800 and separately replaced. Likewise, when the multiple electrode or the controller 710 of the device 700 need to be replaced, they can be individually separated from the device 700 and separately replaced.

The detailed effects of the present invention are made apparent by following tests.

EXPERIMENTAL EXAMPLES

The effects of motion artifacts generated during daily movements and exercise on baseline drift of the electrode according to the present invention and the conventional electrode are comparatively evaluated.

Experimental Example 1

Evaluation of Effects of Turning Body on Baseline Drift

Figure 9:
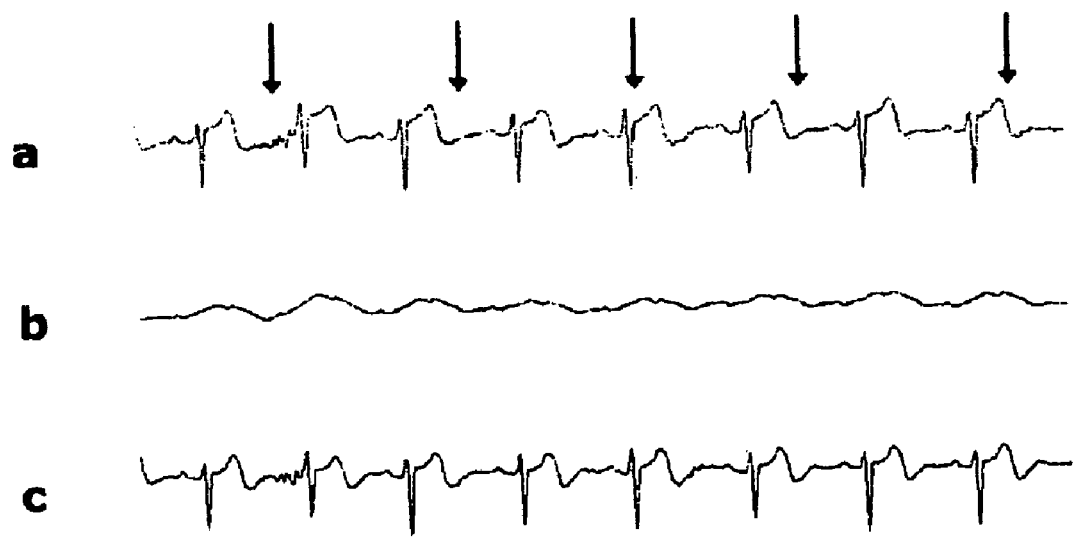
FIG. 9(a) is an original electrocardiograph signal measured by the electrode of the present invention when a patient is turning his/her body.
FIG. 9(b) is a baseline drift component of the original electrocardiograph signal.
FIG. 9(c) is the electrocardiograph signal after the baseline drift component has been removed.
Figure 10:
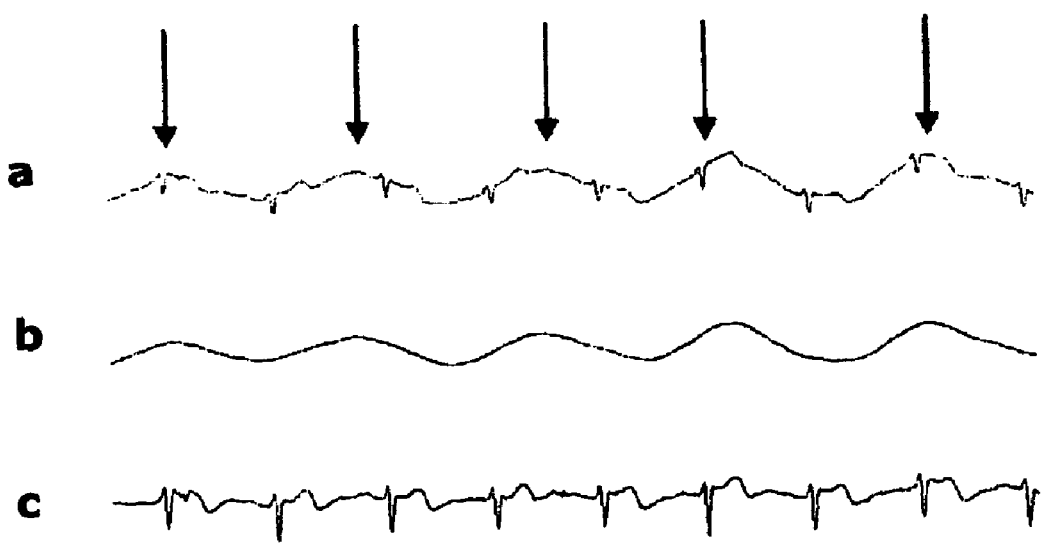
FIG. 10(a) is an original electrocardiograph signal measured by a conventional electrode when a patient is turning his/her body.
FIG. 10(b) is a baseline drift component of the original electrocardiograph signal.
FIG. 10(c) is the electrocardiograph signal after the baseline drift component has been removed.

After an electrode (40 mm in diameter) according to the present invention is attached to a subject and after a conventional electrode (10 mm in diameter) is attached to the same subject, the electrocardiogram signals of the subject are measured while the subject periodically turns his/her body. The measurement results of the electrode of the present invention and the conventional electrode are shown in FIGS. 9 and 10, respectively. In FIGS. 9 and 10, the vertical axis (not shown) denotes the electric potential of the electrocardiogram signal and a horizontal axis (not shown) denotes time. In each drawing, graph 'A' is the original electrocardiogram signal, graph 'B' is the baseline drift component of the original signal, and graph 'C' is an electrocardiogram signal after the baseline drift component has been removed. Arrows of the graph 'A' denote the points of time when the subject starts to turn his/her body. The baseline drift is extracted from the measured original electrocardiogram signal by the use of a mean filter (window size=160 and sampling rate=500 Hz) (graph 'B'). As shown in graphs 'B' of FIGS. 9 and 10, the average and the standard deviation of the baseline drift of the electrode according to the present invention are 0.00134 V and ±0.11325 V (graph 'B' of FIG. 9), and the average and the standard deviation of the baseline drift of the conventional electrode are 0.000619 V and ±1.80232 V (graph 'B' of FIG. 10). The results of the standard deviation are shown in the above Table 1. As shown in Table 1, the electrode according to the present invention is more robust against the motion artifacts due to the turning of body than the conventional electrode.

Experimental Example 2

Evaluation of Effects of Walking at a Speed of 4 km/h on Baseline Drift

Figure 11:
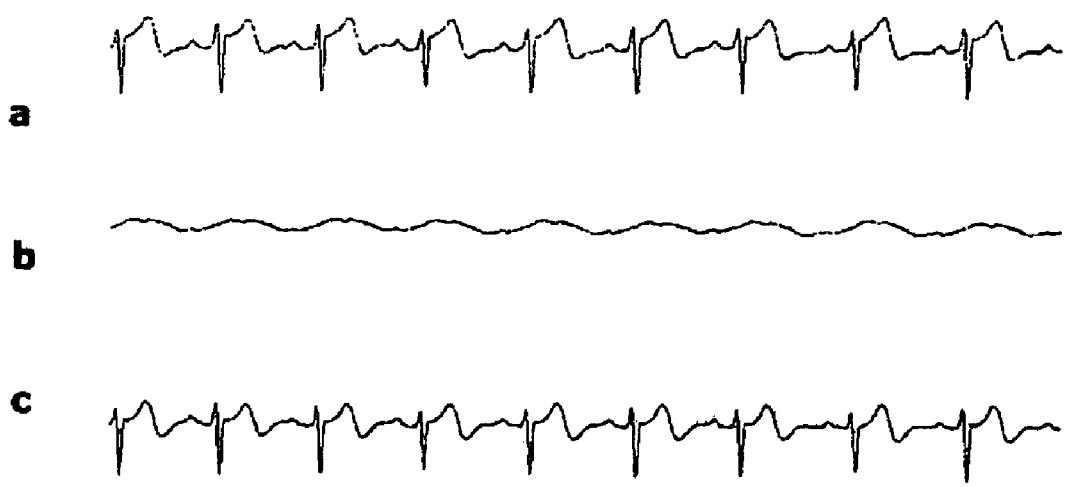
FIG. 11(a) is an original electrocardiograph signal measured by the electrode of the present invention when a patient is walking at 4 km per hour.
FIG. 11(b) is a baseline drift component of the original electrocardiograph signal.
FIG. 11(c) is the electrocardiograph signal after the baseline drift component has been removed.
Figure 12:
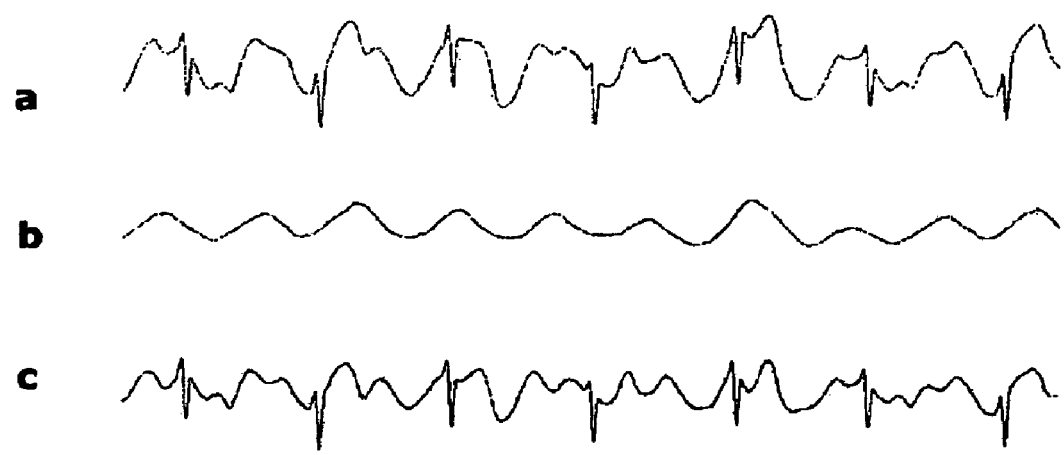
FIG. 12(a) is an original electrocardiograph signal measured by a conventional electrode when a patient is walking at 4 km per hour.
FIG. 12(b) is a base line drift component of the original electrocardiograph signal.
FIG. 12(c) is the electrocardiograph signal after the baseline drift component has been removed.

Experimental Example 2 is performed in the same manner as Experimental Example 1 except that motion artifacts are generated while walking at a speed of 4 km/h instead of periodically turning the body. The testing results are shown in FIGS. 11 and 12. The average and the standard deviation of the baseline drift of the electrode according to the present invention are 0.00081 V and ±0.10074 V (graph 'B' of FIG. 11) and the average and the standard deviation of the baseline drift of the conventional electrode are 0.00048 V and ±0.29 V (graph 'B' of FIG. 12). The results of the standard deviation are shown in the above Table 1. As shown in Table 1, the electrode according to the present invention is more robust against the motion artifacts due to walking at a speed of 4 km/h than the conventional electrode.

Experimental Example 3

Evaluation of Effects of Walking at a Speed of 6 km/h on Baseline Drift

Figure 13:
FIG. 13(a) is an original electrocardiograph signal measured by the electrode of the present invention when a patient is walking at 6 km per hour.
FIG. 13(b) is a baseline drift component of the original electrocardiograph signal.
FIG. 13(c) is the electrocardiograph signal after the baseline drift component has been removed.
Figure 14:
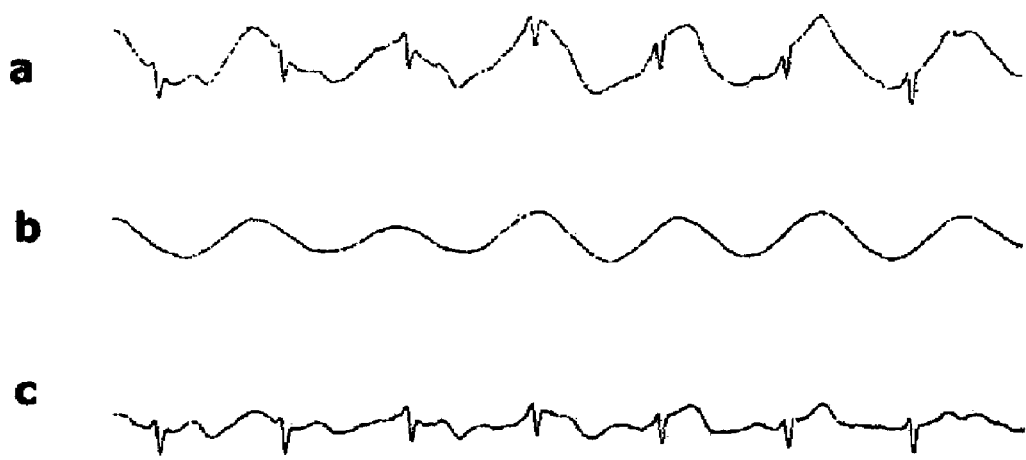
FIG. 14(a) is an original electrocardiograph signal measured by a conventional electrode when a patient is walking at 6 km per hour.
FIG. 14(b) is a baseline drift component of the original electrocardiograph signal.

Experimental Example 3 is performed in the same manner as Experimental Example 1 except that motion artifacts are generated while walking at a speed of 6 km/h instead of periodically turning the body. The testing results are shown in FIGS. 13 and 14. The average and the standard deviation of the baseline drift of the electrode according to the present invention are 0.00217 V and ±0.1108 V (graph 'B' of FIG. 13), and the average and the standard deviation of the baseline drift of the conventional electrode are 0.001 V and ±0.53356 V (graph 'B' of FIG. 14). The results of the standard deviation are shown in the above Table 1. As shown in Table 1, the electrode according to the present invention is more robust against the motion artifacts due to walking at a speed of 6 km/h than the conventional electrode.

Experimental Example 4

Evaluation of Effects of Running at a Speed of 8 km/h on Baseline Drift

Figure 15:
FIG. 15(a) is an original electrocardiograph signal measured by the electrode of the present invention when a patient is running at 8 km per hour.
FIG. 15(b) is a baseline drift component of the original electrocardiograph signal.
FIG. 15(c) is the electrocardiograph signal after the baseline drift component has been removed.
Figure 16:
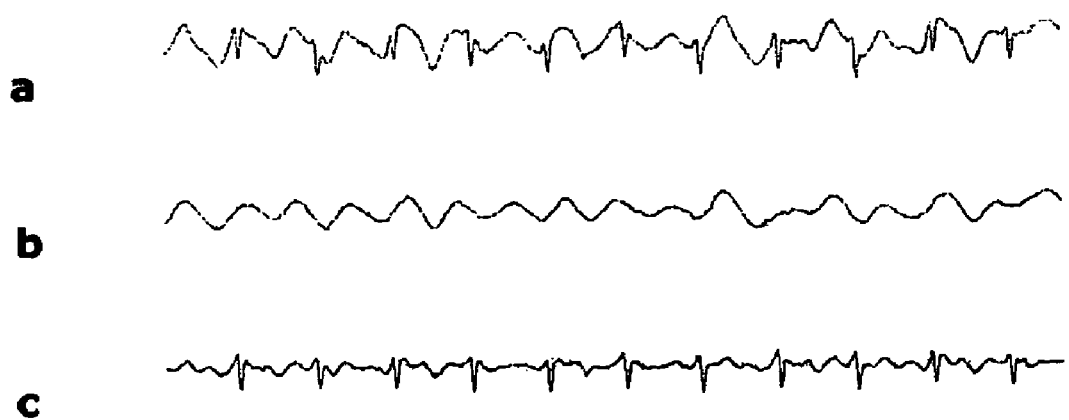
FIG. 16(a) is an original electrocardiograph signal measured by a convention electrode when a patient is running at 8 km per hour.
FIG. 16(b) is a baseline drift component of the original electrocardiograph signal.
FIG. 16(c) is the electrocardiograph signal after the baseline drift component has been removed.

Experimental Example 4 is performed in the same manner as Experimental Example 1 except that motion artifacts are generated while running at a speed of 8 km/h instead of periodically turning the body and using the mean filter having a window size of 70 instead of window size of 160. The reason why the window size is adjusted is that since frequencies of the baseline drift produced by the vibrations due to running overlap the frequency components of a cardiac signal, it is difficult to completely separate a drift signal from the original electrocardiogram signal, and as the subject runs faster, the heartbeat is faster, which results in overlapping of P-waves and T-waves. The testing results are shown in FIGS. 15 and 16. The average and the standard deviation of the baseline drift of the electrode according to the present invention are 0.00217 V and ±0.12086 V (graph 'B' of FIG. 15), and the average and the standard deviation of the baseline drift of the conventional electrode are 0.00447 V and ±0.4781 V (graph 'B' of FIG. 16). The results of the standard deviation are shown in the above Table 1. As shown in Table 1, the electrode according to the present invention is more robust against the motion artifacts due to running at a speed of 8 km/h than the conventional electrode.

According to the present invention, an electrode for measuring an electrocardiogram includes a signal detector formed on the whole surface of the electrode, and thus is robust against motion artifacts and achieves good signal quality. Further, by using electrolytic gel with excellent adhesion and conductivity between the electrode and the skin, the electrode enhances the quality of the signal, alleviates discomfort when the electrode is detached from the skin and does not damage the skin when the electrode is used for a long period of time. Accordingly, the electrode can be used during daily movements or exercise. Moreover, when an electrocardiogram measuring device including the electrode according to the present invention in which elements are integrally formed in the device is used while being attached to the human body, the elements, such as the electrode and a controller, or the electrode, a controller and power supply, can be independently separated from the device only when the electrode or a power supply needs to be replaced.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An electrode for measuring an electrocardiogram comprising:
    a signal detector operable to detect an electrocardiogram signal;
    an electrolytic gel coated onto a first surface of the signal detector, the gel being electrically conductive and operable to adhere to a skin; and
    a controller connector electrically connected to a second surface of the signal detector,
    wherein the first surface of the signal detector occupies an entire side of the electrode, and wherein the electrolytic gel further comprises: 30 to 70 weight percent of water, 0.5 to 5 weight percent of tartaric acid, 20 to 50 weight percent of concentrated glycerine, 5 to 10 weight percent of sodium polyacrylate, and 1 to 6 weight percent of polyethylene glycol.

2. The electrode of claim 1, wherein the signal detector is made of a material selected from the group consisting of platinum, gold, silver, copper, and palladium.

3. An electrode for measuring an electrocardiogram comprising:
a signal detector operable to detect an electrocardiogram signal;
an electrolytic gel coated onto a first surface of the signal detector, the gel being electrically conductive and operable to adhere to a skin; and
a controller connector electrically connected to the signal detector;
wherein the electrolytic gel further comprises:
30 to 70 weight percent of water, 0.5 to 5 weight percent of tartaric acid, 20 to 50 weight percent of concentrated glycerine, 5 to 10 weight percent of sodium polyacrylate, and 1 to 6 weight percent of polyethylene glycol.

4. An electrode for measuring an electrocardiogram comprising:
a signal detector operable to detect an electrocardiogram signal;
an electrolytic gel coated onto a first surface of the signal detector, the gel being electrically conductive and operable to adhere to a skin;
a controller connector electrically connected to the signal detector; and
an adhesive portion which has one surface coated with an adhesive material, the adhesive portion being connected to a second surface of the signal detector, and the adhesive portion having a larger area than the signal detector;
wherein the electrolytic gel further comprises: 30 to 70 weight percent of water, 0.5 to 5 weight percent of tartaric acid, 20 to 50 weight percent of concentrated glycerine, 5 to 10 weight percent of sodium polyacrylate, and 1 to 6 weight percent of polyethylene glycol.

5. The electrode of claim 4, wherein the adhesive portion is made of non-woven fabric.

6. An electrode for measuring an electrocardiogram comprising:
an adhesive portion having a surface coated with an adhesive material operable to be attached to the skin;
a plurality of signal detectors disposed apart from each other, each of said plurality of signal detectors having a first surface connected to the surface of the adhesive portion, said first surface of the signal detector having a smaller area than the adhesive portion;
electrolytic gel coated on a second surface of each signal detector, the electrolytic gel operable to adhere to the skin and being electrically conductive; and
a plurality of controller connectors electrically connected to the respective plurality of signal detectors,
wherein the electrolytic gel comprises:
30 to 70 weight percent of water, 0.5 to 5 weight percent of tartaric acid, 20 to 50 weight percent of concentrated glycerine, 5 to 10 weight percent of sodium polyacrylate, and 1 to 6 weight percent of polyethylene glycol.

7. The electrode of claim 6, wherein the adhesive portion is made of non-woven fabric.

8. The electrode of claim 6, wherein each of the signal detectors is made of a material selected from the group consisting of platinum, gold, silver, copper, and palladium.

9. An electrocardiogram measuring device comprising:
an electrode, said electrode further including:
an adhesive portion having a surface coated with an adhesive material operable to be attached to the skin;
a plurality of signal detectors disposed apart from each other, each of said plurality of signal detectors having a first surface connected to the surface of the adhesive portion, said surface of the signal detector having a smaller area than the adhesive portion;
an electrolytic gel coated on a second surface of each signal detector, the electrolytic gel operable to adhere to the skin and being electrically conductive; and
a plurality of controller connectors electrically connected to the respective plurality of signal detectors,
the electrocardiogram measuring device further comprising:
a controller having a plurality of electrode connectors detachably electrically connected to respective plurality of controller connectors of the electrode,
wherein the electrolytic gel further comprises: 30 to 70 weight percent of water, 0.5 to 5 weight percent of tartaric acid, 20 to 50 weight percent of concentrated glycerine, 5 to 10 weight percent of sodium polyacrylate, and 1 to 6 weight percent of polyethylene glycol.

10. The electrocardiogram measuring device of claim 9, wherein the controller includes a power supply.

11. The electrocardiogram measuring device of claim 9, wherein the controller includes a signal transceiver.

12. The electrocardiogram measuring device of claim 9, wherein a circuit board of the controller is a flexible printed circuit board (PCB).

13. An electrocardiogram measuring device comprising:
an electrode, said electrode further comprising:
an adhesive portion having a surface coated with an adhesive material to be attached to the skin;
a plurality of signal detectors disposed apart from each other, each of said plurality of signal detectors having a first surface connected to the surface of the adhesive portion, said surface of the signal detector having a smaller area than the adhesive portion;
electrolytic gel coated on a second surface of each signal detector, the electrolytic gel adhering to the skin and being electrically conductive; and
a plurality of controller connectors electrically connected to the respective signal detectors,
the electrocardiogram measuring device further comprising:
a controller having a plurality of electrode connectors detachably electrically connected to the respective plurality of controller connectors of the electrode and a power supply connector; and
a power supply having a controller connector detachably electrically connected to the power supply connector of the controller,
wherein the electrolytic gel further comprises: 30 to 70 weight percent of water, 0.5 to 5 weight percent of tartaric acid, 20 to 50 weight percent of concentrated glycerine, 5 to 10 weight percent of sodium polyacrylate, and 1 to 6 weight percent of polyethylene glycol.

14. The electrocardiogram measuring device of claim 13, wherein the controller includes a signal transceiver.

15. The electrocardiogram measuring device of claim 13, wherein a circuit board of each of the controller and the power supply is a flexible printed circuit board (PCB).

16. An electrolytic gel for use in a an electrocardiogram, the gel comprising:

30 to 70 weight percent of water, 0.5 to 5 weight percent of tartaric acid, 20 to 50 weight percent of concentrated glycerine, 5 to 10 weight percent of sodium polyacrylate, and 1 to 6 weight percent of polyethylene glycol.

* * * * *